United States Patent [19]
Fowler et al.

[11] Patent Number: 4,842,746
[45] Date of Patent: Jun. 27, 1989

[54] METHOD OF REMOVING TOXIC AGENTS FOR TRICHLOROTRIFLUOROETHANE

[75] Inventors: David E. Fowler; Eugene T. McIlvaine, both of Gainesville, Fla.

[73] Assignee: Quadrex Hps Inc., Gainesville, Fla.

[21] Appl. No.: 874,679

[22] Filed: Jun. 16, 1986

[51] Int. Cl.⁴ .............................................. B01D 15/00
[52] U.S. Cl. .................................... 210/689; 210/690; 570/179
[58] Field of Search ............... 210/690, 282, 288, 290, 210/679, 689; 570/179

[56] References Cited

U.S. PATENT DOCUMENTS

| | | | |
|---|---|---|---|
| 3,152,077 | 10/1964 | Kryzer | 210/282 |
| 3,327,859 | 6/1967 | Pall | 210/282 |
| 4,046,939 | 9/1977 | Hart | 210/525 |

Primary Examiner—Ivars Cintins
Attorney, Agent, or Firm—Bernard A. Reiter; Mark G. Bocchetti

[57] ABSTRACT

Disclosed is a method of and apparatus for removing chemical nerve agents such as tabun, sarin and soman and chemical blister agents such as mustard gas and lewisite from a cleaning solvent such that the solvent is rendered contaminant free and safely reusable in future cleaning operations. The solvent, trichlorotrifluoroethane and the contaminants are soluble in one another and are all of non-polar configuration. Removal is effected by preferential adsorption of the contaminants from the solvent. Effective adsorbents are Fuller's Earth, activated charcoal, activated alumina and silica gel.

8 Claims, 1 Drawing Sheet

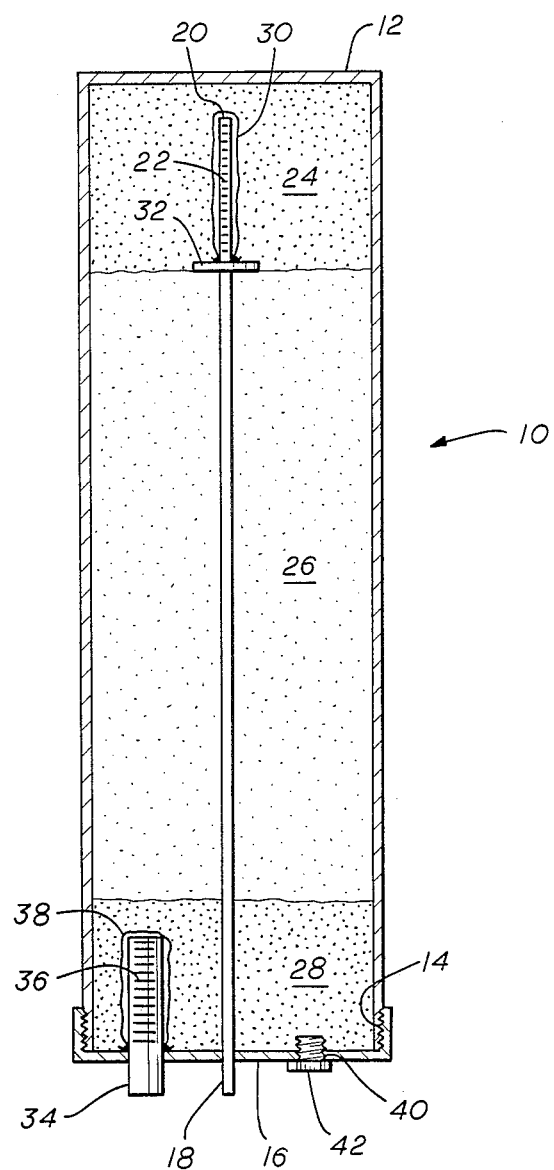

METHOD OF REMOVING TOXIC AGENTS FOR TRICHLOROTRIFLUOROETHANE

BACKGROUND OF THE INVENTION

1. FIELD OF THE INVENTION

The present invention relates generally to the removal of contaminants from a cleaning solvent and particularly to adsorbing chemical nerve and blister agents dissolved in trichlorotrifluoroethane.

2. BRIEF DESCRIPTION OF THE PRIOR ART

Chemical nerve and blister agents of the type which may be encountered in chemical warfare, can be removed from the articles which they contaminate by means of a cleaning solvent. Trichlorotrifluoroethane is a cleaning solvent which can be used for that purpose. Tabun, sarin, soman, lewisite and mustard are all contaminants that are soluble in trichlorotrifluoroethane. Therefore, the use of trichlorotrifluoroethane as a cleaning solvent is effective in removing such contaminants from a contaminated article. However, upon completion of cleaning of the contaminated article, one is left with a contaminated solvent which is, therefore, unfit for reuse since it contains contaminants which would be redeposited on any articles being cleaned if such solvent was reused in cleaning operations. Removing the contaminants from the solvent allows the reuse of the trichlorotrifluoroethane, or other solvent. Further, removal minimizes the volume of contaminated liquid which must be ultimately disposed of and increases economy of operation since disposal is expensive.

A variety of processes dealing with the removal of one fluid from another by adsorption can be found in the prior art. None, however, deal with the removal of chemical nerve and blister agents from trichlorotrifluoroethane as addressed by the present invention and therefore, none can offer the solution of the present invention. On such prior art reference is U.S. Pat. No. 4,498,992 to Garrett, Jr. which appears to teach a method for reconditioning and reclaiming transformer insulating oil. Garrett, Jr. relies on Fuller's Earth for the removal of acidic and oxidized materials typically found in used dielectric fluid. It is obvious that the acidic and oxidized compounds of the Garrett, Jr. patent are in no way related to chemical nerve and blister agents of the type found in chemical warfare, nor is there relation to the invention herein for the removal of these contaminants from the carrier.

U.S. Pat. No. 4,053,571 to Ebner et al teaches a process for purifying lithium hexafluoroarsenate, an electrolite for use in batteries. As part of the Ebner et al process, impurities are removed by using an adsorbent, activated alumina, to selectively adsorb the impurities, e.g. $LiAsF_5$, OH and HF. There is no relation here to the present invention wherein chemical nerve and blister agents are to be removed from the carrier solvent trichlorotrifluoroethane.

U.S. Pat. N. 2,203,690 to Malm et al teaches a process by which chlorinated hydrocarbon contaminants are removed from alcohols or ketones by adsorption using activated charcoal as the adsorbent. As with the prior art references previously mentioned, the Malm et al reference offers nothing useful in the removal of chemical nerve and blister agents from trichlorotrifluoroethane.

U.S. Pat. No. 2,388,616 to La Lande Jr. teaches the use of adsorbents such as silica gel, activated alumina, activated carbon and Fuller's Earth as dehumidification agents. The use of such adsorbents to remove moisture from fluids teaches nothing related to the adsorption of chemical nerve and blister agents from trichlorotrifluoroethane. In fact, it should be recognized that the removal of moisture constitutes the removal of a molecule of polar configuration from a nonpolar carrier.

BRIEF SUMMARY OF THE INVENTION

In the present invention chemical nerve agents and chemical blister agents of the type which may be used in chemical warfare are removed from a cleaning solvent such as trichlorotrifluoroethane, by means of adsorption. Tabun, sarin and soman are all nerve agents and, as noted above, soluble in trichlorotrifluoroethane. Lewisite and mustard gas are blister agents, also noted to be soluble in trichlorotrifluoroethane. Each of such contaminants is of nonpolar configuration. Trichlorotrifluoroethane is also nonpolar in nature. The invention reveals, suprisingly, that such contaminants can be preferentially adsorbed from trichlorotrifluoroethane despite the fact that the contaminants and the solvents are all nonpolar.

Accordingly, it is an object of the present invention to provide a method of and apparatus for removing chemical nerve agents including tabun, sarin and soman from a dry cleaning solvent.

Another object of the present invention is to provide a method of and apparatus for removing chemical blister agents such as mustard and lewisite from a cleaning solvent.

Yet another object of the present invention is to provide a method of and apparatus for removing the chemical nerve and blister agents from a dry cleaning solvent by means of adsorption.

A further object of the present invention is to provide a method of and apparatus for removing chemical nerve and blister agents from a dry cleaning solvent such that the resultant concentration of such contaminants dissolved in the cleaning solvent is less than on part per million, thereby insuring that the solvent can be reused for cleaning purposes without creating a health hazard.

Briefly stated, the foregoing and numerous other features, objects and advantages of the present invention will become readily apparent upon reading the detailed description, claims and drawings set forth hereinafter. These features, objects and advantages are accomplished by adsorption of the contaminating chemical nerve and blister agents from the dry cleaning solvent, trichlorotrifluoroethane, such contaminants being in solution with the dry cleaning solvent. The adsorbents which have been found to perform adequately in this process include Fuller's Earth, activated alumina, activated carbon and silica gel.

Understanding that each of the contaminants named herein is soluble in trichlorotrifluoroethane and that all of such contaminants and trichlorotrifluoroethane are nonpolar in configuration, it is particularly surprising that such contaminants can be preferentially adsorbed from trichlorotrifluoroethane. In fact, understanding such circumstances, it was believed that adsorption would not work.

Other nonpolar configured solvents from which the contaminants named herein may be removed by adsorption include:
Ethanol
Methanol Isopropyl Alcohol
Methylene Chloride
Acetone
Nitro Methane
Freon ® 11

However, the process of the present invention has not bee tested with these solvents.

The contaminants to which the present invention is directed are highly toxic by ingestion, inhalation and/or skin adsorption. The toxicity is so great that exposure to such contaminants even in the parts per million range can be fatal. Such being the case, it is imperative that if the cleaning solvent is to be reused in cleaning operations, if must be effectively decontaminated to a level such that there is less than one part per million of contaminants in the solvent. Adsorption of chemical nerve and blister agents from trichlorotrifluoroethane using Fuller's Earth, activated charcoal, activated alumina, and/or silica gel as the adsorbent accomplishes this absolute requirement.

BRIEF DESCRIPTION OF THE DRAWINGS

FIG. 1 is a vertical cross sectional view of an apparatus of the present invention.

DESCRIPTION OF THE PREFERRED EMBODIMENT

Turning to FIG. 1 there is shown, a cross section of an apparatus for adsorbing chemical nerve and blister agents from trichlorotrifluoroethane, such apparatus contained in cylindrical canister 10. Cylindrical canister 10 has a closed end 12 and an open end 14. Open end 14 is threaded for receiving cover 16. Inlet tube 18 passes through cover 16 along the cylindrical axis of canister 10. Inlet tube 18 extends into canister 10 such that its distal end 20 resides in close proximity to closed end 12 of canister 10.

That portion of inlet tube 18 proximate to distal end 20 has a slots or perforations 22 along its length for allowing contaminated solvent to flow out of inlet tube 18 and into canister 10.

Within canister 10 there resides three layers of adsorbents 24, 26 and 28. Adsorbent layers 24 and 28 are 4Å molecular sieve. Adsorbent layers 24 and 28 function to remove any moisture which may be present in the contaminated solvent thereby protecting adorbent layer 26 from exposure to such moisture. Adsorbent layer 26 is preferably a layer of silica gel specially treated by coating with a metallic salt such as copper sulfate, copper chloride, iron sulfate, or iron chloride. Activated alumina, activated carbon and/or Fuller's Earth may also be the adsorbent making up adsorbent layer 26. Adsorbent layers 24 and 28 are not required when treated silica gel is used for adsorbent layer 26.

If adsorbent layer 26 is comprised of silica gel, it is preferable that such material be 6 to 16 mesh granular. Further, to enhance to adsorptive characteristics of such material it is necessary to soak the silica gel in an aqueous solution saturated with a metallic salt such as copper sulfate, copper chloride, iron sulfate, or iron chloride for at least one hour. The treated silica gel must then be dried for 12 to 24 hours at 150° centigrade. After drying it is necessary to protect the silica gel from exposure to moisture including atmospheric humidity. Silica gel has a high affinity for moisture which will degrade its performance.

If adsorbent layer 26 is comprised of Fuller's Earth, it is preferable that such material be 40 to 60 mesh granular. Further, it is good practice to pre-dry such material before placing it in canister 10. Heating the Fuller's Earth to 100° C. for a period of one hour should be effective for the purpose of pre-drying. It is necessary to protect Fuller's Earth from exposure to too much moisture because as the moisture content of Fuller's earth increases, it will lose its adsorptive quality. Adsorbent layers 24 and 28 furnish this protection.

That portion of inlet tube 18 which contains slots or perforations 22 is covered with a one micron nylon filter cloth 30 to prevent the molecular sieve of adsorbent layer 24 from clogging slots or perforations 22. Located approximately at the inner face of adsorbent layer 24 and adsorbent layer 26 is ring 22. Ring 22 is washer-like and is affixed to inlet tube 18 about the circumference of inlet tube 18. Ring 32 prevents the short circuiting of contaminated solvent through canister 10 along the outside of inlet tube 18.

Also extending through cover 16 substantially parallel to inlet tube 18 is outlet tube 34. That portion of outlet tube 34 residing in canister 10, is completely engulfed within adsorbent layer 28. As with inlet tube 18, outlet tube 34 contains slots or perforations 36. The slotted or perforated portion of outlet tube 34 is covered with a one micron nylon filter cloth 38 which prevents adsorbent layer 28 from clogging slots or perforations 36 or flowing through slots of perforations 36 and exiting canister 10. Cover 16 is also provided with fill port 40 in which threaded plug 42 resides.

In order to place adsorbent layers 24, 26 and 28 within canister 10, it is, of course, necessary to invert the apparatus from that position which is depicted in FIG. 1. Threaded plug 42 is then removed from fill port 40 and the desired quantities of adsorbents for layers 24, 26 and 28 are then poured through fill port 40 in sequence.

The placing of inlet tube 18 such that it extends up into adsorbent layer 24 prevents the flow of contaminated solvent through slots or perforations 22 from eroding adsorbent layer 24 such that flow of contaminated solvent could be directly into adsorbent layer 26. If the inlet tube 18 entered canister 10 through closed end 12 and did not have slots or perforations 28, it is quite likely that the downward force exerted by the flow of contaminated solvent would erode or dish out adsorbent layer 24 in such manner that adsorbent layer 24 would be totally ineffective in protecting adsorbent layer 26 from any incoming moisture.

In operation, contaminated solvent flows through inlet tube 18 and exists inlet tube 18 via slots or perforations 22. Moisture contained in the contaminated solvent is removed by the molecular sieve of adsorbent layer 24. As the contaminated solvent flows through adsorbent layer 26, chemical nerve and blister agents are preferentially adsorbed by such layer thereby allowing only effectively pure solvent to enter adsorbent layer 28 and exit canister 10 via outlet tube 34.

As stated previously, the preferential adsorption of tabun ($(CH_3)_2NP(O)(C_2H_5O)(CN)$), soman ($(CH_3)_3CCH(CH_3)OPF(O)CH_3$) and sarin ($[(CH_3)_2CHO](CH_3$-$FPO)$ is a totally unexpected and beneficial result. Such is also the case with the preferential adsorption of mustard gas (dichlorodiethyl sulfide) and lewisite (beta-chlorovinyldichloroarsine) from trichlorotrifluoroethane. All of such contaminants are soluble in trichlorotrifluoroethane and all are nonpolar in configuration as is trichlorotrifluoroethane.

From the foregoing, it will be seen that this invention is one well adapted to attain all of the ends and objects hereinabove set forth, together with other advantages which are obvious and which are inherent to the apparatus and method.

It will be understood that certain features and subcombinations are of utility and may be employed with reference to other features and subcombinations. This is contemplated by and is within the scope of the claims.

As many possible embodiments may be made of the invention without departing from the scope thereof it is to be understood that all matter herein set forth or shown in the accompanying drawing is to be interpreted as illustrative and not in a limiting sense.

What is claimed is:

1. A process for removing chemical nerve agents and chemical blister agents from trichlorotrifluoroethane and from mixtures of solvents wherein trichlorotrifluoroethane is a constituent thereof comprising:

conducting a liquid solvent wherein trichlorotrifluoroethane is a constituent thereof having chemical nerve agents selected from the group consisting of tabun, sarin and soman and chemical blister agents selected from the group consisting of lewisite and mustard agent dissolved therein through an absorbent selected from the group consisting of Fuller's Earth, activated carbon, activated alumina, silica gel, and silica gel coated with a metallic salt, said adsorbent preferentially adsorbing the chemical nerve and blister agents.

2. A process for removing chemical nerve agents and chemical blister agents from trichlorotrifluoroethane and from mixtures of solvents wherein trichlorotrifluoroethane is a constituent thereof as recited in claim 1, further comprising:

circulating said trichlorotrifluoroethane through a molecular sieve means for removal of moisture prior to said conducting step thereby preventing any water from reaching said adsorbent.

3. A process for removing chemical nerve agents and/or chemical blister agents from trichlorotrifluoroethane comprising the steps of:

(a) conducting trichlorotrifluoroethane having chemical nerve and blister agents selected from the group consisting of tabun, sarin, soman, lewisite, and mustard agent dissolved therein through an adsorbent selected from the group consisting of Fuller's Earth, activated carbon, activated alumina and silica gel, said adsorbent preferentially adsorbing the chemical nerve and blister agents;

(b) collecting said trichlorotrifluoroethane exiting said adsorbent, said trichlorotrifluoroethane exiting said adsorbent containing less than one part per million of chemical nerve and blister agents.

4. A process for removing chemical nerve agents and/or chemical blister agents from trichlorotrifluoroethane as recited in claim 1 or 3, wherein: said adsorbent is a 40–40 mesh granular, predried Fuller's Earth.

5. A process for removing chemical nerve agents and/or chemical blister agents from trichlorotrifluoroethane comprising the steps of:

(a) conducting trichlorotrifluoroethane having chemical nerve and blister agents selected from the group consisting of tabun, sarin, soman, lewisite, and mustard agent dissolved therein through silica gel which is coated with a metallic salt, said silica gel coated with a metallic salt preferentially adsorbing the chemical nerve and blister agent;

(b) collecting said trichlorotrifluoroethane exiting said silica gel, said trichlorotrifluoroethane exiting said adsorbent containing less than one part per million of chemical nerve and blister agents.

6. A process for decontaminating trichlorotrifluoroethane having chemical and/or blister agents dissolved therein comprising the steps of:

conducting contaminated trichlorotrifluoroethane through and adsorbent, said adsorbent selected from the group consisting of Fuller's Earth, activated carbon, activated alumina, and silica gel, said adsorbent preferentially adsorbing the chemical nerve and blister agents selected from the group consisting of tabun, sarin, soman, lewisite, and mustard gas dissolved in said contaminated trichlorotrifluoroethane thereby rendering the effluent from said adsorbent effectively free of chemical nerve and blister agent contamination.

7. A process for removing chemical nerve agents and chemical blister agents from trichlorotrifluoroethane and from solvents which contain trichlorotrifluoroethane as a constituent thereof comprising the steps of:

(a) conducting the solvent which includes trichlorotrifluoroethane as a constituent thereof having chemical nerve agents dissolved therein selected from the group consisting of tabun, sarin, and soman, and chemical blister agents dissolved therein selected from the group consisting of lewisite and mustard agent, through an adsorbent, said adsorbent preferentially adsorbing said chemical nerve agents and said chemical blister agents.

8. A process for removing chemical nerve agents and chemical blister agents from trichlorotrifluoroethane comprising the steps of:

conducting contaminated trichlorotrifluoroethane through an adsorbent, the contaminated trichlorotrifluoroethane being contaminated with chemical nerve agents selected from the group consisting of tabun, sarin and soman, and chemical blister agents selected from the group consisting of lewisite and mustard agent, said adsorbent preferentially adsorbing said chemical nerve agents and said chemical blister agents, said adsorbent selected from the group consisting of Fuller's Earth, activated carbon, activated alumina, silica gel and silica gel coated with a metallic salt.

* * * * *